(12) United States Patent
Ochiya

(10) Patent No.: US 12,013,399 B2
(45) Date of Patent: *Jun. 18, 2024

(54) METHOD OF EXOSOME ANALYSIS, REAGENT FOR EXOSOME ANALYSIS, AND ANALYZER FOR EXOSOME

(71) Applicant: THEORIA Science Inc., Tokyo (JP)

(72) Inventor: Takahiro Ochiya, Tokyo (JP)

(73) Assignee: THEORIA Science Inc., Tokyo (JP)

( * ) Notice: Subject to any disclaimer, the term of this patent is extended or adjusted under 35 U.S.C. 154(b) by 205 days.

This patent is subject to a terminal disclaimer.

(21) Appl. No.: 17/830,991

(22) Filed: Jun. 2, 2022

(65) Prior Publication Data

US 2022/0299517 A1    Sep. 22, 2022

Related U.S. Application Data

(63) Continuation of application No. 14/367,651, filed as application No. PCT/JP2012/077621 on Oct. 25, 2012, now Pat. No. 11,391,741.

(30) Foreign Application Priority Data

Dec. 22, 2011    (JP) ................................. 2011-281618

(51) Int. Cl.
*G01N 33/53* (2006.01)
*G01N 33/50* (2006.01)
*G01N 33/574* (2006.01)

(52) U.S. Cl.
CPC ... *G01N 33/57492* (2013.01); *G01N 33/5076* (2013.01); *G01N 33/57434* (2013.01); *G01N 2333/70596* (2013.01)

(58) Field of Classification Search
CPC ......... G01N 33/57492; G01N 33/5076; G01N 33/57434; G01N 2333/70596
See application file for complete search history.

(56) References Cited

U.S. PATENT DOCUMENTS 7,897,356 B2    3/2011    Klass et al.
2009/0220944 A1    9/2009    Fais et al.

FOREIGN PATENT DOCUMENTS

WO    00/17643    3/2000
WO    2009/092386    7/2009
WO    2010/056337    5/2010
WO    2012/048372    4/2012

OTHER PUBLICATIONS

PerkinElmer, "AlphaLISA immunoassays: the no-wash alternative to ELISAs for research and drug discovery", Nature Methods, Dec. 2008, an8/an9.
Office Action issued in corresponding European Patent Application No. 12860743.9, dated Jun. 23, 2016, 7 pages.
Extended European Search Report issued in the corresponding European Patent Application No. 12860743.9 dated Jun. 2, 2015 (6 pages).
Taylor et al., "MicroRNA signatures of tumor-derived exosomes as diagnostic biomarkers of ovarian cancer", Gynecologic Oncology, vol. 110, pp. 13-21 (2008).
Cauchon et al., "Development of a homogeneous immunoassay for the detection of angiotensin I in plasma using AlphaLISA acceptor beads technology," Analytical Biochemistry, vol. 388, No. 1, pp. 134-139 (2009).
Bosse, "Principles of AlphaScreen Amplified Luminescent Proximity Homogenous Assay", Application Note, Perkin Elmer Life Sciences (www.perkinelmer.com/CMSResources/images/APP_AlphaScreen_Principles.pdf), 2002, 8 pages.
Eglen, et al., "The Use of AlphaScreen Technology in HTS: Current Status", Current Chemical Genomics, 2008, I, pp. 2-10.
Poulsen, et al., "A Luminescent Oxygen Channeling Immunoassay for the Determination of Insulin in Human Plasma", Journal of Biomolecular Screening 12(2), 2007, 240-247.

*Primary Examiner* — Carmencita M Belei
(74) *Attorney, Agent, or Firm* — HSML P.C.

(57) ABSTRACT

The present invention is to provide a method of exosome analysis that can analyze exosome in a sample in a simple manner.
The method of exosome analysis of the present invention is a method of analyzing exosome in a sample, including: an addition step of adding a first antibody that specifically binds to a first antigen contained in the exosome and a second antibody that specifically binds to a second antigen contained in the exosome to the sample; a reaction step of causing the first antigen to be reacted with the first antibody and the second antigen to be reacted with the second antibody; and a detection step of detecting a reaction between the first antigen and the first antibody and a reaction between the second antigen and the second antibody.

3 Claims, 6 Drawing Sheets

METHOD OF EXOSOME ANALYSIS, REAGENT FOR EXOSOME ANALYSIS, AND ANALYZER FOR EXOSOME

TECHNICAL FIELD

The present invention relates to a method of exosome analysis, a reagent for exosome analysis, and an analyzer for exosome.

BACKGROUND ART

In the clinical field, for cancer diagnoses, for example, tumor-associated antigens (the so-called tumor markers) that are characteristically expressed on cancer cells are used. For the analysis of such tumor markers, analysis methods using antibodies that specifically bind to tumor markers are employed.

On the other hand, it has been reported that the amount of exosome in blood of ovarian cancer patients increases as the cancer becomes more advanced (Non-Patent Document 1).

RELATED ART DOCUMENT

Non-Patent Document

[Non-Patent Document 1] Taylor et al., Gynecologic Oncol, 100 (2008) pp. 13-21

DISCLOSURE OF THE INVENTION

Problem to be Solved by the Invention

While the analysis of exosome in blood described in Non-Patent Document 1 is conducted by analyzing specific microRNA (miRNA) expressed on exosome, miRNA analysis requires complicated operations.

Hence, the present invention is intended to provide a method of exosome analysis, a reagent for exosome analysis, and an analyzer for exosome that can analyze exosome in a simple manner.

Means for Solving Problem

The method of exosome analysis of the present invention is a method of analyzing exosome in a sample, including:
an addition step of adding a first antibody that specifically binds to a first antigen contained in the exosome and a second antibody that specifically binds to a second antigen contained in the exosome to the sample;
a reaction step of causing the first antigen to be reacted with the first antibody and the second antigen to be reacted with the second antibody; and
a detection step of detecting a reaction between the first antigen and the first antibody and a reaction between the second antigen and the second antibody.

The reagent for exosome analysis of the present invention is a reagent used for analysis of exosome in a sample, including:
a first antibody that specifically binds to a first antigen contained in the exosome; and
a second antibody that specifically binds to a second antigen contained in the exosome, wherein the reagent is used for the analysis method of the present invention.

The analyzer for exosome of the present invention is an analyzer for exosome in a sample, including:
an addition unit adding a first antibody that specifically binds to a first antigen contained in the exosome and a second antibody that specifically binds to a second antigen contained in the exosome to the sample;
a reaction unit causing the first antigen to be reacted with the first antibody and causing the second antigen to be reacted with the second antibody; and
a detection unit detecting a reaction between the first antigen and the first antibody and a reaction between the second antigen and the second antibody, wherein the analyzer is used for the analysis method of the present invention.

Effects of the Invention

According to the present invention, exosome in a sample can be analyzed in a simple manner. Therefore, for example, the analysis method of the present invention is very useful to cancer diagnoses such as whether or not a cancer has occurred, whether or not a cancer has recurred, and the like; and application of the analysis method of the present invention to laboratory testing is expected. Further, with the reagent for exosome analysis and the analyzer for exosome of the present invention, the analysis method of the present invention can be conducted efficiently.

DESCRIPTION OF EMBODIMENTS

Exosome Analysis Method

Figure 1A:
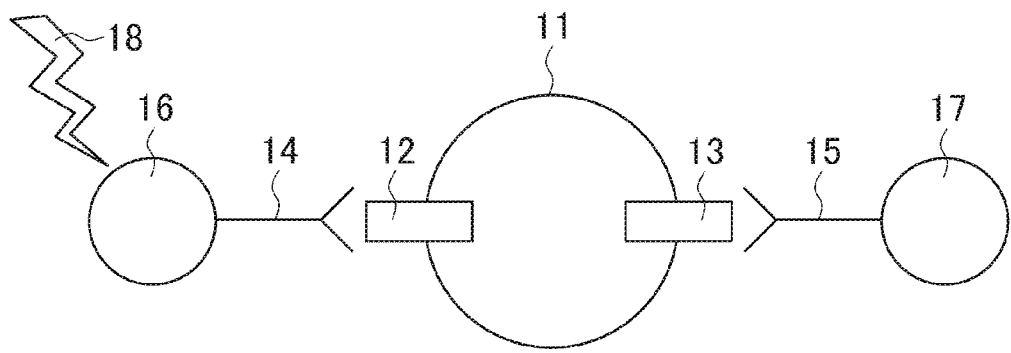
FIG. 1A is a schematic view for explaining an example of the analysis method of the present invention.

The method of exosome analysis of the present invention is, as described above, a method of analyzing exosome in a sample, including: an addition step of adding a first antibody that specifically binds to a first antigen contained in the exosome and a second antibody that specifically binds to a second antigen contained in the exosome to the sample; a reaction step of causing the first antigen to be reacted with the first antibody and the second antigen to be reacted with the second antibody; and a detection step of detecting a reaction between the first antigen and the first antibody and a reaction between the second antigen and the second antibody.

There is no particular limitation on the sample, and examples thereof include biological samples. There is no particular limitation on the biological sample, and examples thereof include blood, urine, sweat, saliva, breast milk, semen, lymph, cerebrospinal fluid, and tears. Examples of the blood sample include whole blood, blood serum, and blood plasma. Among them, blood serum is particularly preferable.

The sample is preferably a liquid specimen because the liquid specimen is easy to handle, for example. With respect to the sample, for example, a specimen that has not been diluted can be used directly as a liquid specimen or a diluent obtained by suspending, dispersing, or dissolving a specimen in a solvent can be used as a liquid specimen. In the case where the specimen is solid, for example, a diluent obtained by suspending, dispersing, or dissolving the specimen in a solvent can be used as a liquid specimen. There is no particular limitation on the solvent, and examples thereof include water and buffer solutions. There is no particular limitation on the buffer solutions, and examples thereof include conventionally known buffer solutions. Further, for example, the sample can be prepared by preparing exosome from the blood or the like by ultracentrifugation or the like and adding the solvent thereto.

There is no particular limitation on the amount of the sample to be used, and the amount of the sample to be used is, for example, in the range from 1 to 15 µL. According to the present invention, for example, exosome can be analyzed with a small amount of sample. The amount of the sample to be used is preferably in the range from 1 to 10 µL and more preferably in the range from 1 to 5 µL.

The exosome is a membrane vesicle covered with a lipid bilayer membrane having a diameter of 30 to 100 nm secreted from an animal cell and contains antigens. According to the present invention, exosome in a sample is analyzed utilizing two antigens (the first antigen and the second antigen) contained in the exosome. Therefore, exosome in a sample can be analyzed in a simple manner. The analysis may be a qualitative analysis, a quantitative analysis, or a semi-quantitative analysis, for example.

Examples of the first antigen and second antigen contained in exosome include an antigen specifically expressed on the exosome (hereinafter also referred to as "exosome-specific antigen") and an antigen specific to a cell that secretes the exosome (hereinafter also referred to as "cell type-specific antigen"). As the combination of the first antigen and second antigen, there are the following three examples (1) to (3).
(1) first antigen: exosome-specific antigen
second antigen: exosome-specific antigen
(2) first antigen: exosome-specific antigen
second antigen: cell type-specific antigen
(3) first antigen: cell type-specific antigen
second antigen: exosome-specific antigen Examples of the exosome-specific antigen include CD63, CD9, CD81, CD37, CD53, CD82, CD13, CD11, CD86, ICAM-1, Rab5, Annexin V, and LAMP1. The cell type-specific antigen can be decided appropriately according to the type of the cell to be analyzed using exosome, for example. In the case where the cell is a cancer cell, the cell type-specific antigen can be, for example, a cancer cell-specific antigen, and examples thereof include Caveolin-1, EpCAM, FasL, TRAIL, Galectine3, CD151, Tetraspanin 8, EGFR, HER2, RPN2, CD44, and TGF-β. The cell is not limited to the cancer cell, and examples thereof include cells associated with diseases involving exosome. Specifically, examples of the cell include cells related to a neurodegenerative disease such as Alzheimer, an immunodeficiency related disease, infertility, mental disorders such as depression and autism, an intractable disease such as Parkinson's disease, an autoimmune disease, a rheumatic disease, and an allergic disease. The cell type-specific antigen is not limited to the cancer cell-specific antigen, and can be antigens that are specifically expressed on cells associated with the aforementioned diseases involving exosome, for example.

As described above, the first antibody is an antibody that specifically binds to the first antigen and the second antibody is an antibody that specifically binds to the second antigen. Examples of the first antibody and second antibody include immunoglobulin (Ig), antibody fragments, and chimeric antibodies. Examples of the immunoglobulin include IgG, IgA, IgM, IgE, and IgD. Examples of the antibody fragment include Fab, Fab', and F(ab')2. Examples of the chimeric antibody include humanized antibodies. There is no particular limitation on the antibody, and the antibody can be one derived from animal species such as mammals such as mice, rabbits, cattle, pigs, horses, sheep, and goats; birds such as chickens; and human. The antibodies can be prepared from blood serum derived from the animal species by conventionally known methods, for example, or commercially available antibodies can be used. The antibody can be, for example, either a polyclonal antibody or a monoclonal antibody, and is preferably the monoclonal antibody.

The first antibody is preferably an antibody that is bindable to an excitation label that is excited by excitation light. In this case, the second antibody is preferably an antibody that is bound to a signaling label that emits a signal by singlet oxygen generated by the excitation of the excitation label. The excitation label is a label that is bindable to the first antibody and excited by excitation light. The excitation label is preferably an excitation carrier, and a specific example thereof includes an excitation carrier produced by PerkinElmer (the so-called "donor beads"). There is no particular limitation on the wavelength of the excitation light that excites the excitation label, and the wavelength can be determined appropriately according to the type and the like of the excitation label. There is no particular limitation on the combination scheme of the first antibody and the excitation label, and for example, there is a scheme of binding a biotinylated antibody as the first antibody to a streptavidin-coated label as the excitation label. The biotinylation of the first antibody can be performed by conventionally known methods, and specifically, for example, the biotinylation of the first antibody can be performed by the method described in the Example described below. As the streptavidin-coated label, for example, "AlphaScreen streptavidin donor beads (Streptavidin-coated Alpha Donor Beads)" produced by PerkinElmer can be used.

The signaling label emits a signal by singlet oxygen generated by the excitation of the excitation label. The signaling label is preferably a signaling carrier. The signal is preferably a fluorescence signal. Specifically, an example of such a signaling label includes "AlphaLISA Acceptor Beads" (the so-called "acceptor beads") produced by PerkinElmer. There is no particular limitation on the method of binding the second antibody and the signaling label, and for example, the binding can be performed by the method described in the Example described below.

In the analysis method of the present invention, conventionally known additives can be contained in a reaction solution within a range that does not interfere with the analysis of exosome. However, in the analysis method of the present invention, preferably, the analysis of exosome is conducted in a reaction solution that does not contain surfactants. An example of the surfactant includes Triton X-100. The reason for the above is that there is a case where the analysis accuracy of exosome is decreased due to the surfactant contained in the reaction solution, for example. For preventing the surfactant from being contained in the reaction solution, preferably, the surfactant is not used at the time of preparing the sample, the first antibody, and the second antibody.

With respect to the analysis method of the present invention, three exemplary analysis methods of Embodiments 1 to 3 will be described below. However, the present invention is not limited to the following Embodiments. The analysis method of Embodiment 1 is an Embodiment in which antibodies that bind to exosome-specific antigens are used as the first antibody and the second antibody. The analysis method of Embodiment 2 is an Embodiment in which an antibody that binds to an exosome-specific antigen is used as the first antibody and an antibody that binds to a cell type-specific antigen is used as the second antibody. The analysis method of Embodiment 3 is an Embodiment in which an antibody that binds to a cell type-specific antigen is used as the first antibody and an antibody that binds to an exosome-specific antigen is used as the second antibody. In the analysis methods of Embodiments 1 to 3, the first antibody is an antibody that is bindable to the excitation label and the second antibody is an antibody that is bound to the signaling label, the excitation label is added in the addition step, and blood serum is used as the sample.

Embodiment 1

First, the analysis method of Embodiment 1 will be described. In the analysis method of Embodiment 1, as described above, antibodies that bind to exosome-specific antigens are used as the first antibody and the second antibody; and the addition step, the reaction step, and the detection step are performed.

First, the first antibody, the second antibody, and the excitation label are added to the blood serum sample. While there is no particular limitation on the order of the addition of the composition, preferably, the first antibody and the second antibody are added in advance, the resultant is incubated, and then the excitation label is added thereto, for example.

Next, the reaction step and the detection step will be described with reference to the schematic view of FIG. 1A.

As shown in FIG. 1A, exosome-specific antigens 12 and 13 are expressed on an exosome 11. In a reaction solution, a first antibody 14 and a second antibody 15 respectively bind to the exosome-specific antigens 12 and 13 contained in the exosome 11 in a blood serum sample. Further, an excitation label 16 binds to the first antibody 14. When the excitation label 16 is excited by excitation light 18, singlet oxygen is generated. Here since the first antibody 14 and the second antibody 15 respectively bind to the exosome-specific antigens 12 and 13, the excitation label 16 and a signaling label 17 are close to each other. Therefore, a signal is emitted from the signaling label 17 by the singlet oxygen. This signal is detected in the detection step.

Embodiment 2

Next, the analysis method of Embodiment 2 will be described. In the analysis method of Embodiment 2, as described above, an antibody that binds to an exosome-specific antigen is used as the first antibody and an antibody that binds to a cell type-specific antigen is used as the second antibody; and the addition step, the reaction step, and the detection step are performed.

First, the first antibody, the second antibody, and the excitation label are added to the blood serum sample. While there is no particular limitation on the order of the addition of the composition, preferably, the first antibody and the second antibody are added in advance, the resultant is incubated, and then the excitation label is added thereto, for example.

Next, the reaction step and the detection step will be described with reference to the schematic view of FIG. 1B.

Figure 1B:
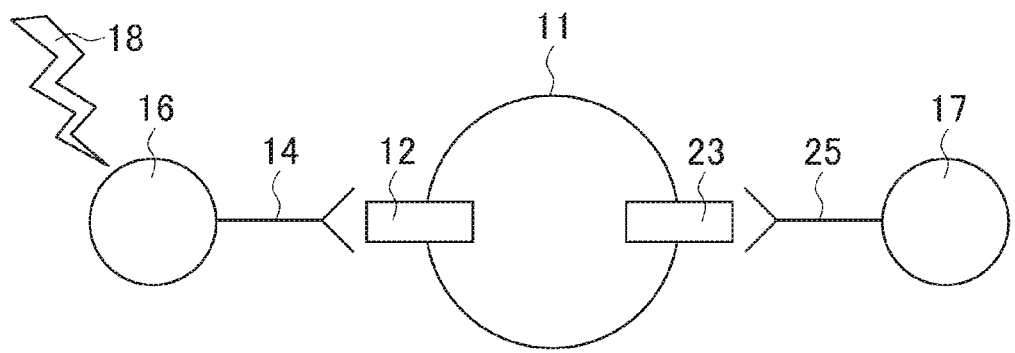
FIG. 1B is a schematic view for explaining another example of the analysis method of the present invention.

As shown in FIG. 1B, an exosome-specific antigen 12 and a cell type-specific antigen 23 are expressed on an exosome 11. In a reaction solution, a first antibody 14 binds to the exosome-specific antigen 12 contained in the exosome 11 in the blood sample. A second antibody 25 binds to the cell type-specific antigen 23 contained in the exosome 11. Further, an excitation label 16 binds to the first antibody 14. When the excitation label 16 is excited by excitation light 18, singlet oxygen is generated. Here since the first antibody 14 binds to the exosome specific antigen 12 and the second antibody 25 binds to the cell type-specific antigen 23, the excitation label 16 and a signaling label 17 are close to each other. Therefore, a signal is emitted from the signaling label 17 by the singlet oxygen. This signal is detected in the detection step.

Embodiment 3

Next, the analysis method of Embodiment 3 will be described. In the analysis method of Embodiment 3, as described above, an antibody that binds to a cell type-specific antigen is used as the first antibody and an antibody that binds to an exosome-specific antigen is used as the second antibody; and the addition step, the reaction step, and the detection step are performed.

First, the first antibody, the second antibody, and the excitation label are added to the blood serum sample. While there is no particular limitation on the order of the addition of the composition, preferably, the first antibody and the second antibody are added in advance, the resultant is incubated, and then the excitation label is added thereto, for example.

Next, the reaction step and the detection step will be described with reference to the schematic view of FIG. 1C.

Figure 1C:
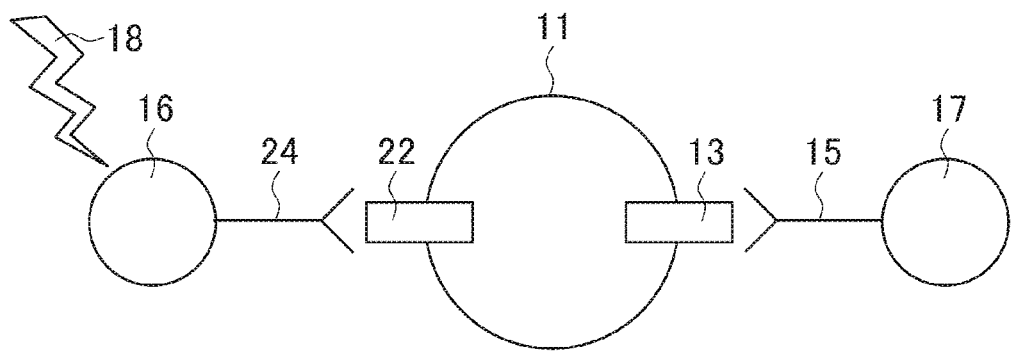
FIG. 1C is a schematic view for explaining yet another example of the analysis method of the present invention.

As shown in FIG. 1C, an exosome-specific antigen 13 and a cell type-specific antigen 22 are expressed on an exosome 11. In a reaction solution, a first antibody 24 binds to the cell type-specific antigen 22 contained in the exosome 11 in the blood sample. A second antibody 15 binds to the exosome-specific antigen 13 contained in the exosome 11. Further, an excitation carrier 16 binds to the first antibody 24. When the excitation carrier 16 is excited by excitation light 18, singlet oxygen is generated. Since the first antibody 24 binds to the cell type-specific antigen 22 and the second antibody 15 binds to the exosome-specific antigen 13, the excitation label 16 and a signaling label 17 are close to each other. Therefore, a signal is emitted from the signaling label 17 by the singlet oxygen. This signal is analyzed in the detection step.

The analysis method of the present invention may further include a correction step of correcting a detection value detected in the detection step, for example. In the correction step, for example, the detection value can be corrected by the correlation between the detection value and the concentration of exosome in a sample. The correlation can be obtained, for example, by detecting a detection value of a standard sample whose exosome concentration is known in the same manner as the present invention and plotting the detection value of the sample and the detection value of the standard sample. The standard sample is preferably a dilution series of exosome. By performing the correction in this manner, the detection can be achieved with higher reliability. Preferably, the exosome contained in the sample and the exosome contained in the standard sample are the ones secreted from cells of the same type (for example, cancer cells of the same type).

[Reagent for Exosome Analysis]

The reagent for exosome analysis of the present invention is, as described above, a reagent used for analysis of exosome in a sample, including: a first antibody that specifically binds to a first antigen contained in the exosome; and a second antibody that specifically binds to a second antigen contained in the exosome, wherein the reagent is used for the analysis method of the present invention. The description for the analysis method of the present invention can also be applied to the reagent for exosome analysis of the present invention.

[Analyzer for Exosome]

The analyzer for exosome of the present invention is, as described above, an analyzer for exosome in a sample, including: an addition means (unit) adding a first antibody and a second antibody to the sample; a reaction means (unit) causing a first antigen to be reacted with the first antibody and causing a second antigen to be reacted with the second antibody; and a detection means (unit) detecting a reaction between the first antigen and the first antibody and a reaction between the second antigen and the second antibody, wherein the analyzer is used for the analysis method of the present invention. The description for the analysis method of the present invention can also be applied to the analyzer for exosome of the present invention.

The addition means includes: a suction/discharge means provided at the inside or the outside of the analyzer sucking/discharging the first antibody and the second antibody; and a control means controlling the amount of suction/discharge of each component, for example. An example of the suction/discharge means includes a pump. An example of the control means includes a valve. The first antibody and the second antibody are added to the sample by the addition means to prepare a reaction solution.

Examples of the reaction means include means for stirring, sucking/discharging, shaking, and sonicating the reaction solution.

An example of the detection means includes an optical analyzer, and a specific example thereof includes a fluorescence measurement apparatus. The detection means may include an excitation light irradiation means emitting excitation light to a reaction solution, for example.

The aforementioned analysis method of the present invention can be performed with the analyzer of the present invention. While an exemplary usage of the analyzer of the present invention will be described below with reference to a case in which the excitation label and the signaling label are used, the present invention is not limited thereto.

The blood sample, the first antibody, and the second antibody are provided at the inside or the outside of the analyzer.

First, the first antibody, the second antibody, and the excitation label are added to the sample by the addition means. While there is no particular limitation on the order of the addition, preferably, the first antibody and the second antibody are added to the sample in advance, the resultant is incubated, and then the excitation label is added thereto, for example. In this case, preferably, the analyzer of the present invention is provided with an incubator. Then, the reaction solution is irradiated with excitation light from the excitation light irradiation means, and a signal emitted from the signaling label is detected by the detection means. In this manner, with the analyzer of the present invention, the aforementioned analysis method of the present invention can be performed, for example, automatically.

EXAMPLES

Next, Examples of the present invention will be described. The present invention is not limited to the Examples below.

1. Antibody that Binds to Exosome-Specific Antigen

As the antibody that binds to an exosome-specific antigen, the following antibodies (1) to (3) are provided.
(1) Purified Mouse Anti-Human CD63 (BD Biosciences, Clone: H5C6)
(2) Purified Mouse Anti-Human CD9 (BD Biosciences, Clone: M-L13)
(3) Purified Mouse Anti-Human CD81 (BD Biosciences, Clone: JS-81)

2. Biotinylation of Antibody

The antibodies are biotinylated according to the following procedures (1) to (7) to produce biotinylated antibodies.
(1) With respect to the provided antibodies, buffers were substituted using Zeba Spin Desalting columns 7K MWCO (Thermo). Columns were each set in 1.5 mL tube and centrifugation was performed at 1500×g (14700 m/s$^2$) for 1 minute.
(2) After the centrifugation, 300 μL of PBS was added to each of the columns, and centrifugation was performed at 1500×g (14700 m/s$^2$) for 1 minute. The routine of addition of PBS and centrifugation was repeated three times.
(3) The columns each were moved to a new 1.5 mL tube, the antibodies were added thereto, and centrifugation was performed at 1500×g (14700 m/s$^2$) for 2 minutes.
(4) 7.62 μL of ChromaLink Biotin 354S (solulink) having a concentration of 2 mg/mL was added to 100 μL of each of the antibody solutions (PBS) each having a concentration of 1 mg/mL, and 92.38 μL of PBS was added thereto so that the total amount of each solution became 200 μL.
(5) The solutions were incubated in a constant temperature water tank of 23° C. for 2 hours to cause the antibodies to be biotinylated.
(6) New Zeba Spin Desalting columns with which the procedures (1) and (2) have been performed were provided, 100 μL of each of the biotinylated antibodies was added to the column, and centrifugation was performed at 1500×g (14700 m/s$^2$) for 2 minutes.
(7) The concentration and labeling ratio of each of the obtained biotinylated antibodies were calculated, and the final concentration was adjusted to 500 mM (500 mmol/L) in PBS.

3. Confirmation of Biotinylation of Antibody

Figure 2A:
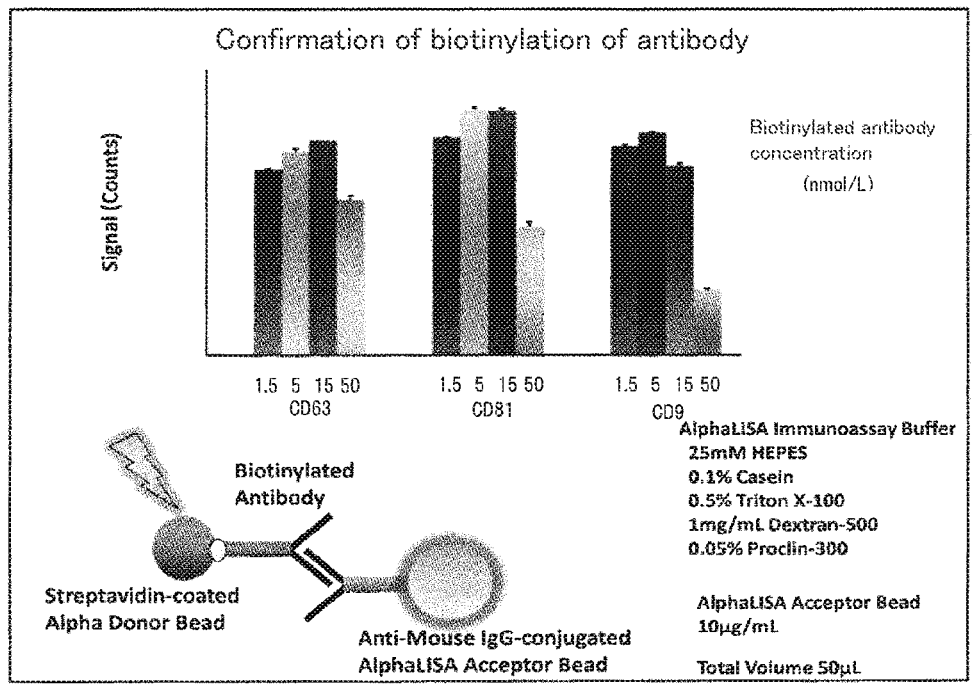
FIG. 2A is a graph showing the result of the confirmation that antibodies are biotinylated in Example of the present invention.

As shown in FIG. 2A, AlphaLISA Acceptor Beads having a concentration of 10 μg/mL were added to AlphaLISA Immunoassay Buffer such that the total amount of the solution became 50 μL, and measurement was performed. As shown in FIG. 2A, the composition of the AlphaLISA Immunoassay Buffer is as follows: 25 mM HEPES, 0.1% casein, 0.5% Triton X-100, 1 mg/mL Dextran-500, and 0.05% ProClin-300. The biotinylation of the antibody was confirmed using Anti-mouse IgG AlphaLISA Acceptor Beads (PerkinElmer) by conducting an assay according to the following procedures (1) to (5).
(1) The biotinylated antibodies were each diluted to 1.5, 5, 15, and 50 nM (nmol/L) using AlphaLISA Immunoassay Buffer (PerkinElmer). In the same manner, Anti-mouse IgG AlphaLISA Acceptor Beads having a concentration of 5 mg/mL were diluted to a 100-fold diluent (concentration of 50 μg/mL) using AlphaLISA Immunoassay Buffer.
(2) 5 μL of AlphaLISA Immunoassay Buffer was added to each well of a 96-well white plate (PerkinElmer, 1/2 AreaPlate-96), and then 10 μL of each of the biotinylated antibodies that have been diluted in the procedure (1) was added thereto. The final concentrations of the biotinylated antibodies were 0.3, 1, 3, and 10 nM (nmol/L), respectively. Further, as a control, 10 μL of PBS was added in place of the diluted biotinylated antibodies (the final concentration of biotinylated antibody: 0 nM (nmol/L)).
(3) Then, 10 μL of Anti-mouse IgG AlphaLISA Acceptor Beads (50 μg/mL) that has been diluted in the procedure (1) was added, and the resultant was incubated at a room temperature in the dark for 1 hour.
(4) AlphaScreen streptavidin donor beads (Streptavidin-coated Alpha Donor Beads) (PerkinElmer) having a concentration of 5 mg/mL were diluted to a 62.5-fold diluent (concentration: 80 μg/mL) using AlphaLISA Immunoassay Buffer. 25 μL of the diluted AlphaScreen streptavidin donor beads (Streptavidin-coated Alpha Donor Beads) was added to each well, which has been incubated, the plate was sealed with TopSeal-A (PerkinElmer), and incubation was performed at room temperature in the dark for 30 minutes.
(5) After the incubation, analysis was conducted using EnSpire (PerkinElmer). The antibodies that bind to exosome-specific antigens are the following three types: Purified Mouse Anti-Human CD63 (BD Biosciences, Clone: H5C6), Purified Mouse Anti-Human CD9 (BD Biosciences, Clone: M-L13), and Purified Mouse Anti-Human CD81. With respect to each of the three antibodies, samples respectively having biotinylated antibody concentrations of 1.5, 5, 15, and 50 nM (nmol/L) were prepared, and signals were analyzed using EnSpire. From this analysis, it was confirmed that the antibodies were biotinylated. The analysis was conducted with the following setting: Measure Technology: AlphaScreen (excitation wavelength: 680 nm, detection wavelength: 520 to 620 nm) (the same applies below). As a result, as shown in FIG. 2A, it was confirmed that the biotinylated antibody that was bound to AlphaLISA Acceptor Beads and the biotinylated antibody that was bound to AlphaScreen streptavidin donor beads (Streptavidin-coated Alpha Donor Beads) were bound to each other.

4. Binding of Antibody to AlphaLISA Acceptor Beads

Figure 2B:
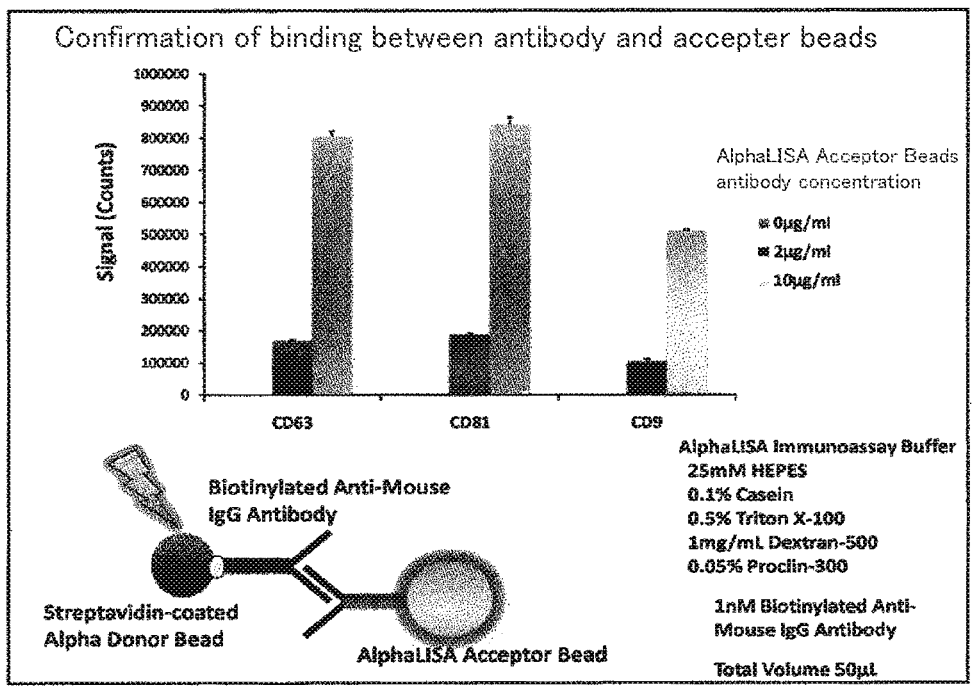
FIG. 2B is a graph showing the result of the confirmation that antibodies are bound to AlphaLISA Acceptor Beads in Example of the present invention.

As shown in FIG. 2B, Biotinylated Anti-Mouse IgG Anitibody having a concentration of 1 nM was added to AlphaLISA Immunoassay Buffer such that the total amount of the solution became 50 μL, and measurement was performed. The composition of AlphaLISA Immunoassay Buffer is as shown in FIG. 2B, i.e., the same as that used in "3. Confirmation of Biotinylation of Antibody" (FIG. 2A). The antibodies were caused to bind to AlphaLISA Acceptor Beads according to the following procedures (1) to (9).
(1) The procedures (1) to (3) in "2. Biotinylation of Antibody" were performed.
(2) 50 μL of Anti-mouse IgG AlphaLISA Acceptor Beads was transferred to a 1.5 mL tube in which the column was set, and centrifugation was performed at 16000×g (156800 m/s$^2$) for 15 minutes. After the centrifugation, the supernatant was removed.
(3) 50 μL of PBS was added to the AlphaLISA Acceptor Beads precipitated after centrifugation, and the resultant was subjected to centrifugation at 16000×g (156800 m/s$^2$) for 15 minutes. After the centrifugation, the supernatant was removed.
(4) 88.75 μL of PBS was added to the AlphaLISA Acceptor Beads precipitated after centrifugation, and the resultant was subjected to vortex to resuspend the precipitated AlphaLISA Acceptor Beads.
(5) 100 μL of each of the antibody solutions (PBS) each having a concentration of 1 mg/mL was added to the suspension, 1.25 μL of 10% Tween-20 and 10 μL of NaBH$_3$CN solution having a concentration of 25 mg/mL were further added thereto, and the resultant was incubated at 37° C. for 24 hours.
(6) 10 μL of carboxymethylamine solution having a concentration of 65 mg/mL (0.8 M (mol/L) NaOH solution) was added to the suspension after incubation, and the resultant was incubated at 37° C. for 1 hour.
(7) The suspension after incubation was subjected to centrifugation at 16000×g (156800 m/s$^2$) for 15 minutes. After the centrifugation, the supernatant was removed, and 200 μL of Tris-HCl (pH 8.0) having a concentration of 0.1 M (mol/L) was added to the precipitate to suspend it. Then, the resultant was subjected to centrifugation in the same manner as described above. This operation was repeated twice to wash.
(8) The suspension after washing was subjected to centrifugation at 16000×g (156800 m/s$^2$) for 15 minutes, and the supernatant was removed. 200 μL of PBS that contains 0.05% ProClin-300 was added to the precipitate to resuspend it. In this manner, antibodies that were bound to AlphaLISA Acceptor Beads (hereinafter also referred to as "acceptor beads-binding antibodies") (final concentration: 5 mg/mL) were prepared. (9) The suspension was subjected to vortex followed by light spindown, and 1 second sonication was performed 20 times using a sonicator. The resultant was preserved at 4° C. in the dark.

5. Confirmation of Binding between Antibody and Acceptor Beads

The binding of the antibodies to AlphaLISA Acceptor Beads was confirmed using Biotin-SP-conjugated AffiniPure Goat Anti-Mouse IgG (H+L) (JacksonImmunoResearch) by conducting an assay according to the following procedures (1) to (5).
(1) The acceptor beads-binding antibodies were each diluted to 10 and 50 μg/mL using AlphaLISA Immunoassay Buffer. In the same manner, the biotinylated antibodies were each diluted to 5 nM (nmol/L) using AlphaLISA Immunoassay Buffer.
(2) 5 μL of AlphaLISA Immunoassay Buffer was added to each well of the 96-well white plate, and then 10 μL of each of the biotinylated antibodies that have been diluted in the procedure (1) was added thereto.
(3) Then, 10 μL of each of the acceptor beads-binding antibodies that have been diluted in the procedure (1) was added, and the resultant was incubated at a room temperature in the dark for 1 hour. As a control, 10 μL of PBS was added in place of the diluted acceptor beads-binding antibodies.
(4) AlphaScreen streptavidin donor beads (Streptavidin-coated Alpha Donor Beads) having a concentration of 5 mg/mL was diluted to a 62.5-fold diluent (concentration: 80 μg/mL) using AlphaLISA Immunoassay Buffer. 25 μL of the diluted AlphaScreen streptavidin donor beads (Streptavidin-coated Alpha Donor Beads) was added to each well, which has been incubated, the plate was sealed with TopSeal-A, and incubation was performed at a room temperature in the dark for 30 minutes.
(5) After the incubation, analysis was conducted using EnSpire. The antibodies that bind to exosome-specific antigens are the following three types: Purified Mouse Anti-Human CD63 (BD Biosciences, Clone: H5C6), Purified Mouse Anti-Human CD9 (BD Biosciences, Clone: M-L13), and Purified Mouse Anti-Human CD81. With respect to each of the three antibodies, samples respectively having AlphaLISA Acceptor Beads antibody concentrations of 0, 2, and 10 μg/mL were prepared and signals were analyzed using EnSpire. From this analysis, it was confirmed that the antibodies were bound to AlphaLISA Acceptor Beads. The analysis was conducted with the following setting: Measure Technology: AlphaScreen. As a result, as shown in FIG. 2B, it was confirmed that the biotinylated antibody (Biotinylated Anti-Mouse IgG Antibody) that was bound to AlphaLISA Acceptor Beads and the biotinylated antibody (Biotinylated Anti-Mouse IgG Antibody) that was bound to AlphaScreen streptavidin donor beads (Streptavidin-coated Alpha Donor Beads) were bound to each other. No signal was observed with respect to the samples each having a AlphaLISA Acceptor Beads antibody concentration of 0 μg/mL.

6. Quantitation of Exosome (Preparation of Exosome)
Exosome was prepared from a cancer cell conditioned medium by ultracentrifugation according to the following procedures (1) to (7).
(1) Prostate cancer cell strain PC3 (purchased from ATCC) was disseminated in a 15 cm dish and cultured.
(2) On the day after the dissemination, the cancer cell was washed with PBS, the culture medium was replaced with Advanced PRMI1640 (Invitrogen) that does not contain blood serum, and the cell was cultured for 2 days.
(3) After the culture, the conditioned medium was collected and subjected to centrifugation at 2000×g (19600 m/s$^2$) for 10 minutes, and the supernatant was collected.
(4) The supernatant was filtrated with a filter (pore size: 0.22 μm).
(5) The filtrate was subjected to centrifugation at 100000×g (980000m/s$^2$) at 4° C. for 70 minutes.
(6) After the centrifugation, the supernatant was removed, PBS was added to the precipitate, and the resultant was subjected to centrifugation at 100000×g (980000m/s$^2$) at 4° C. for 70 minutes.
(7) After the centrifugation, the supernatant was removed, PBS was added to the precipitate, and the resultant was let stand overnight at 4° C. and then subjected to vortex on the next day to collect exosome.
(Making of Calibration Curve)
The quantitative analysis of the collected exosome was performed using the biotinylated antibodies and the acceptor beads-binding antibodies according to the following procedures (1) to (5), and calibration curves of exosome were made. In the following procedures (1) to (4), with respect to AlphaLISA Universal Buffer (PerkinElmer), PBS that contains 0.1% BSA and 0.05% ProClin-300 was used.
(1) Biotinylated antibodies and acceptor beads-binding antibodies were respectively diluted to 5 nM (nmol/L) and 50 μg/mL using AlphaLISA Universal Buffer (PerkinElmer).
(2) The collected exosome was diluted using AlphaLISA Universal Buffer to prepare a dilution series having predetermined concentrations.
(3) 5 μL of the diluted exosome was added to each well of the 96-well white plate. As a control, 5 μL of AlphaLISA Universal Buffer was added, 10 μL of biotinylated antibody having a concentration of 5 nM (nmol/L) and 10 μL of acceptor beads-binding antibody having a concentration of 50 μg/mL were further added thereto, and the resultant was incubated at room temperature in the dark for 1 hour.
(4) AlphaScreen streptavidin donor beads (Streptavidin-coated Alpha Donor Beads) having a concentration of 5 mg/mL was diluted to a 62.5-fold diluent (concentration: 80 μg/mL) using AlphaLISA Immunoassay Buffer. 25 μL of the diluted AlphaScreen streptavidin donor beads (Streptavidin-coated Alpha Donor Beads) was added to each well, which has been incubated, the plate was sealed with TopSeal-A, and incubation was performed at room temperature in the dark for 30 minutes. There is no particular limitation on the incubation time, and, for example, the incubation time can be set in the range from 1 hour to all night according to the change of temperature conditions or the like.
(5) After the incubation, signals were analyzed using EnSpire, and exosome was analyzed. The analysis was conducted with the following setting: Measure Technology: AlphaScreen. Then, calibration curves were made from a dilution series of exosome.

(Result of Making of Calibration Curve)

With respect to the following combinations (1) to (6) of biotinylated antibodies and acceptor beads-binding antibodies, calibration curves were made. The following combinations (1) to (6) of antibodies and the calibration curves thereof are respectively shown in FIGS. 2C to 2H.

(1) biotinylated antibody: Purified Mouse Anti-Human CD63 acceptor beads-binding antibody: Purified Mouse Anti-Human CD63 y=0.0017x ($R^2$=0.9891)
(2) biotinylated antibody: Purified Mouse Anti-Human CD9 acceptor beads-binding antibody: Purified Mouse Anti-Human CD9 y=0.0201x ($R^2$=0.9826)
(3) biotinylated antibody: Purified Mouse Anti-Human CD81 acceptor beads-binding antibody: Purified Mouse Anti-Human CD81 y=0.0186x ($R^2$=0.9985)
(4) biotinylated antibody: Purified Mouse Anti-Human CD63 acceptor beads-binding antibody: Purified Mouse Anti-Human CD9 y=0.0141x ($R^2$=0.996)
(5) biotinylated antibody: Purified Mouse Anti-Human CD9 acceptor beads-binding antibody: Purified Mouse Anti-Human CD81 y=0.0037x ($R^2$=0.9998)
(6) biotinylated antibody: Purified Mouse Anti-Human CD81 acceptor beads-binding antibody: Purified Mouse Anti-Human CD63 y=0.0031x ($R^2$=0.9998)

Figure 2C:
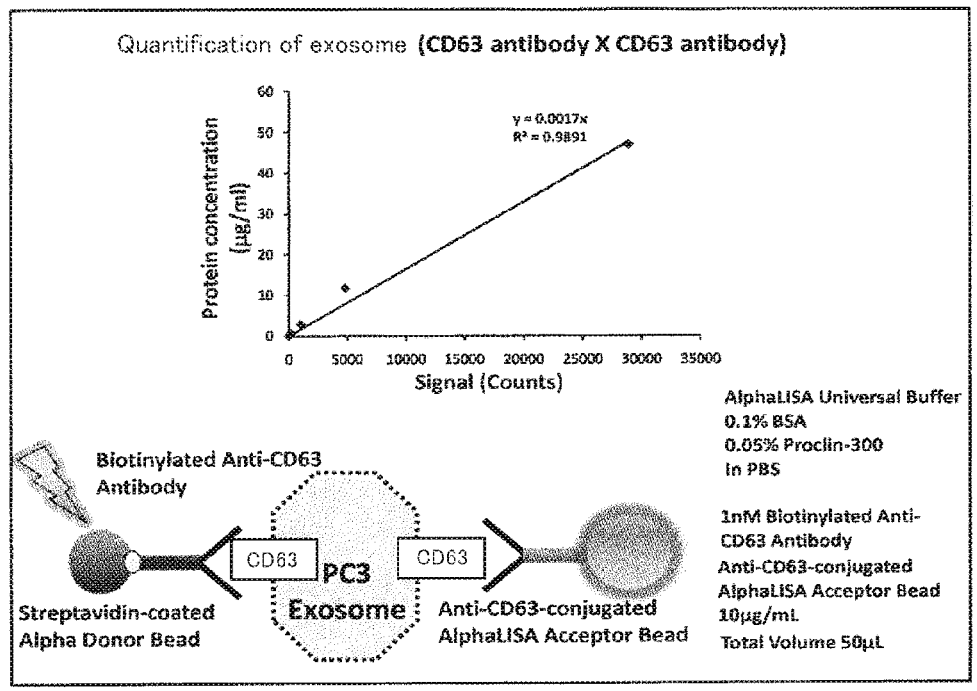
FIG. 2C is a calibration curve used for the quantitative analysis of exosome in Example of the present invention (biotinylated antibody: Purified Mouse Anti-Human CD63, acceptor beads-binding antibody: Purified Mouse Anti-Human CD63).

With respect to FIG. 2C (the combination (1)), in a PBS solution, Biotinylated Anti-CD63 Antibody having a concentration of 1 nM and Anti-CD63-conjugated AlphaLISA Acceptor Beads having a concentration of 10 μg/mL were added to AlphaLISA Universal Buffer that contains 0.1% BSA and 0.05% ProClin-300 such that the total amount of the solution became 50 μL, and measurement was performed. FIG. 2C shows that Biotinylated Anti-CD63 Antibody that is bound to AlphaScreen streptavidin donor beads (Streptavidin-coated Alpha Donor Beads) and Biotinylated Anti-CD63 Antibody that is bound to Anti-CD63-conjugated AlphaLISA Acceptor Beads are each bound to antigen CD63 in PC3 exosome. A calibration curve was made by plotting the signal in a horizontal axis and protein concentration (μg/ml) in a vertical axis, and the following equation was obtained: y=0.0017x ($R^2$=0.9891).

Figure 2D:
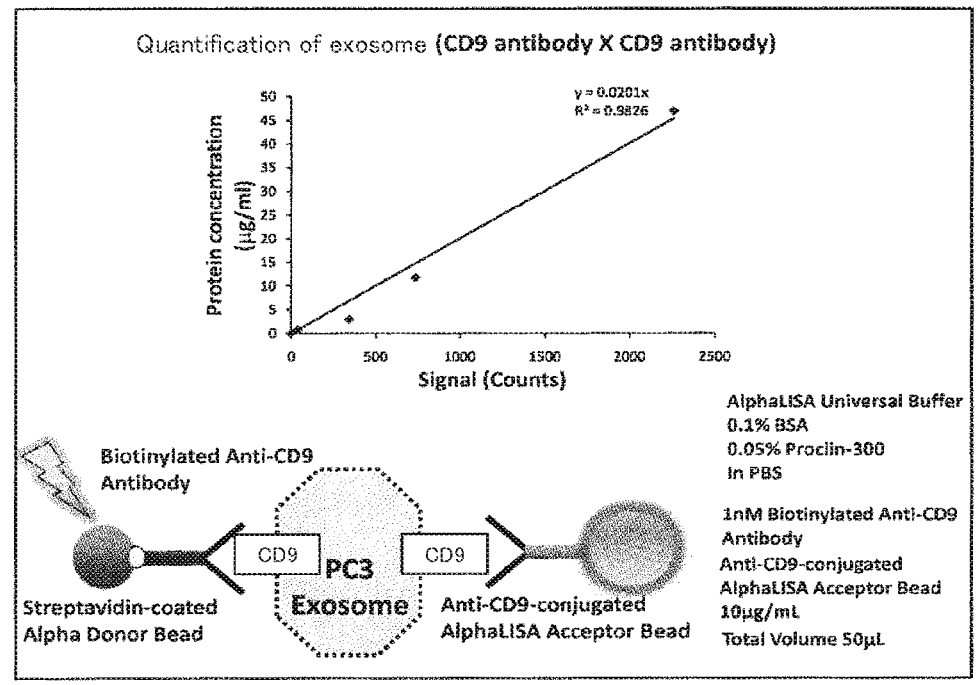
FIG. 2D is a calibration curve used for the quantitative analysis of exosome in Example of the present invention (biotinylated antibody: Purified Mouse Anti-Human CD9, acceptor beads-binding antibody: Purified Mouse Anti-Human CD9).

With respect to FIG. 2D (the combination (2)), Biotinylated Anti-CD9 Antibody having a concentration of 1 nM and Anti-CD9-conjugated AlphaLISA Acceptor Beads having a concentration of 10 μg/mL were added to the aforementioned AlphaLISA Universal Buffer such that the total amount of the solution became 50 μL, and measurement was performed. FIG. 2D shows that Biotinylated Anti-CD9 Antibody that is bound to AlphaScreen streptavidin donor beads (Streptavidin-coated Alpha Donor Beads) and Biotinylated Anti-CD9 Antibody that is bound to Anti-CD9-conjugated AlphaLISA Acceptor Beads are each bound to antigen CD9 in PC3 exosome. A calibration curve was made by plotting signal in a horizontal axis and protein concentration (μg/ml) in a vertical axis, and the following equation was obtained: y=0.0201x ($R^2$=0.9826).

Figure 2E:
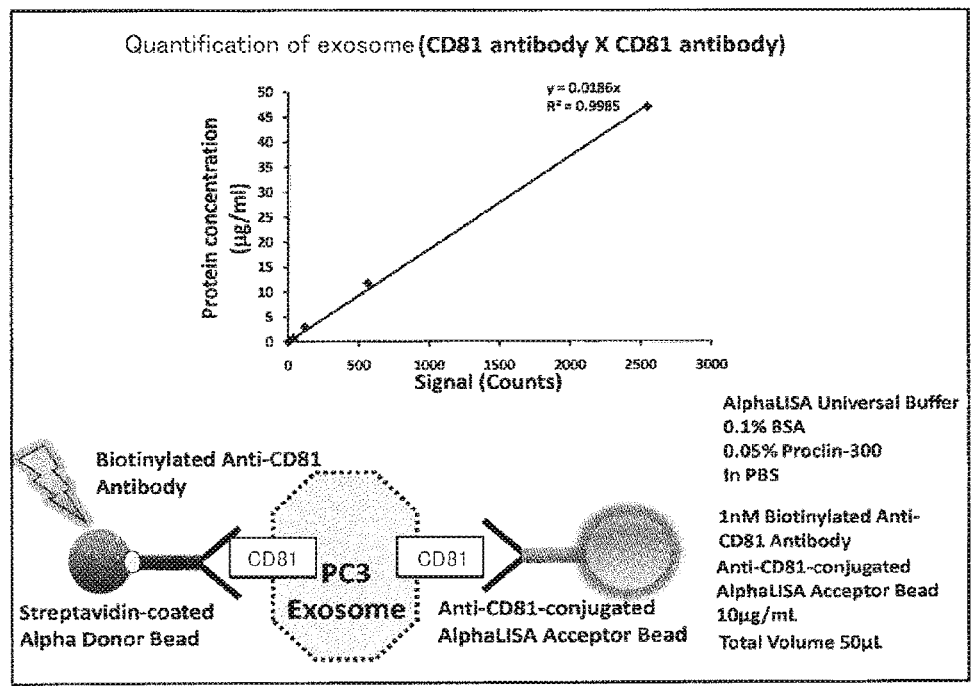
FIG. 2E is a calibration curve used for the quantitative analysis of exosome in Example of the present invention (biotinylated antibody: Purified Mouse Anti-Human CD81, acceptor beads-binding antibody: Purified Mouse Anti-Human CD81).

With respect to FIG. 2E (the combination (3)), Biotinylated Anti-CD81 Antibody having a concentration of 1 nM and Anti-CD81-conjugated AlphaLISA Acceptor Beads having a concentration of 10 μg/mL were added to the aforementioned AlphaLISA Universal Buffer such that the total amount of the solution became 50 μL, and measurement was performed. FIG. 2E shows that Biotinylated Anti-CD81 Antibody that is bound to AlphaScreen streptavidin donor beads (Streptavidin-coated Alpha Donor Beads) and Biotinylated Anti-CD81 Antibody that is bound to Anti-CD81-conjugated AlphaLISA Acceptor Beads are each bound to antigen CD81 in PC3 exosome. A calibration curve was made by plotting the signal in a horizontal axis and protein concentration (μg/ml) in a vertical axis, and the following equation was obtained: y=0.0186x ($R^2$=0.9985).

Figure 2F:
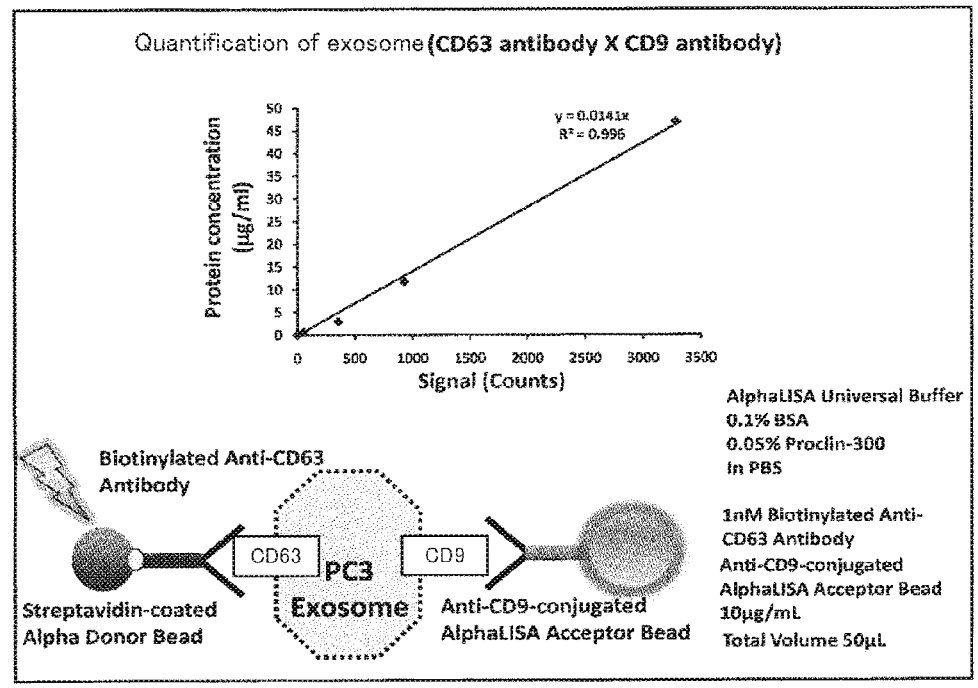
FIG. 2F is a calibration curve used for the quantitative analysis of exosome in Example of the present invention (biotinylated antibody: Purified Mouse Anti-Human CD63, acceptor beads-binding antibody: Purified Mouse Anti-Human CD9).

With respect to FIG. 2F (the combination (4)), Biotinylated Anti-CD63 Antibody having a concentration of 1 nM and Anti-CD9-conjugated AlphaLISA Acceptor Beads having a concentration of 10 μg/mL were added to the aforementioned AlphaLISA Universal Buffer such that the total amount of the solution became 50 μL, and measurement was performed. FIG. 2F shows that Biotinylated Anti-CD63 Antibody that is bound to AlphaScreen streptavidin donor beads (Streptavidin-coated Alpha Donor Beads) and Biotinylated Anti-CD63 Antibody that is bound to Anti-CD9-conjugated AlphaLISA Acceptor Beads are respectively bound to antigen CD63 and antigen CD9 in PC3 exosome. A calibration curve was made by plotting the signal in a horizontal axis and protein concentration (μg/ml) in a vertical axis, and the following equation was obtained: y=0.0141x ($R^2$=0.996).

Figure 2G:
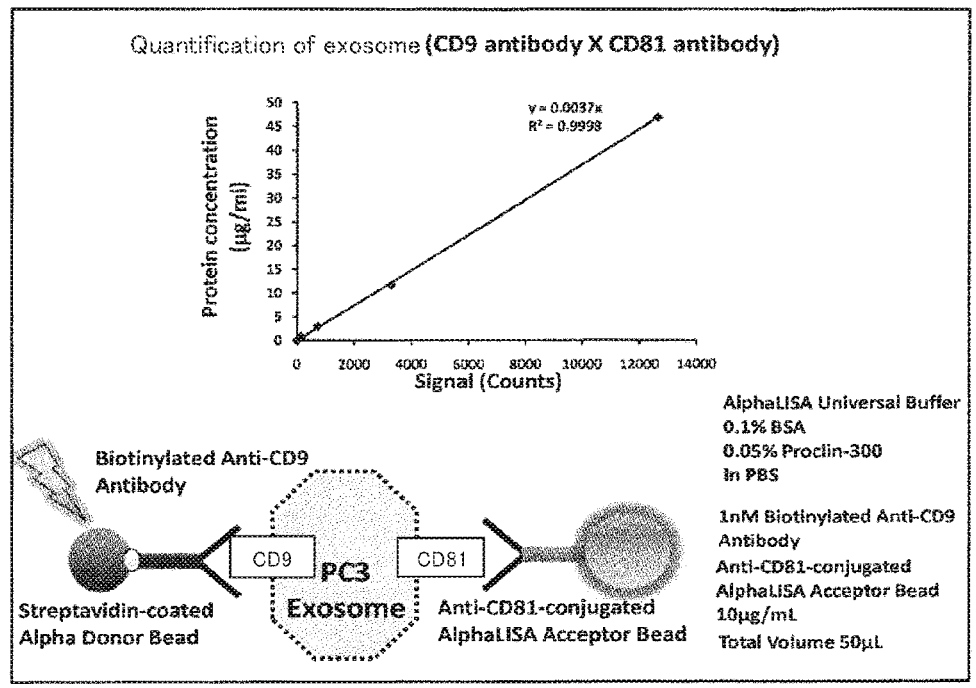
FIG. 2G is a calibration curve used for the quantitative analysis of exosome in Example of the present invention (biotinylated antibody: Purified Mouse Anti-Human CD9, acceptor beads-binding antibody: Purified Mouse Anti-Human CD81).

With respect to FIG. 2G (the combination (5)), Biotinylated Anti-CD9 Antibody having a concentration of 1 nM and Anti-CD81-conjugated AlphaLISA Acceptor Beads having a concentration of 10 μg/mL were added to the aforementioned AlphaLISA Universal Buffer such that the total amount of the solution became 50 μL, and measurement was performed. FIG. 2G shows that Biotinylated Anti-CD9 Antibody that is bound to AlphaScreen streptavidin donor beads (Streptavidin-coated Alpha Donor Beads) and Biotinylated Anti-CD81 Antibody that is bound to Anti-CD81-conjugated AlphaLISA Acceptor Beads are respectively bound to antigen CD9 and antigen CD81 in PC3 exosome. A calibration curve was made by plotting the signal in a horizontal axis and protein concentration (μg/ml) in a vertical axis, and the following equation was obtained: y=0.0037x ($R^2$=0.9998).

Figure 2H:
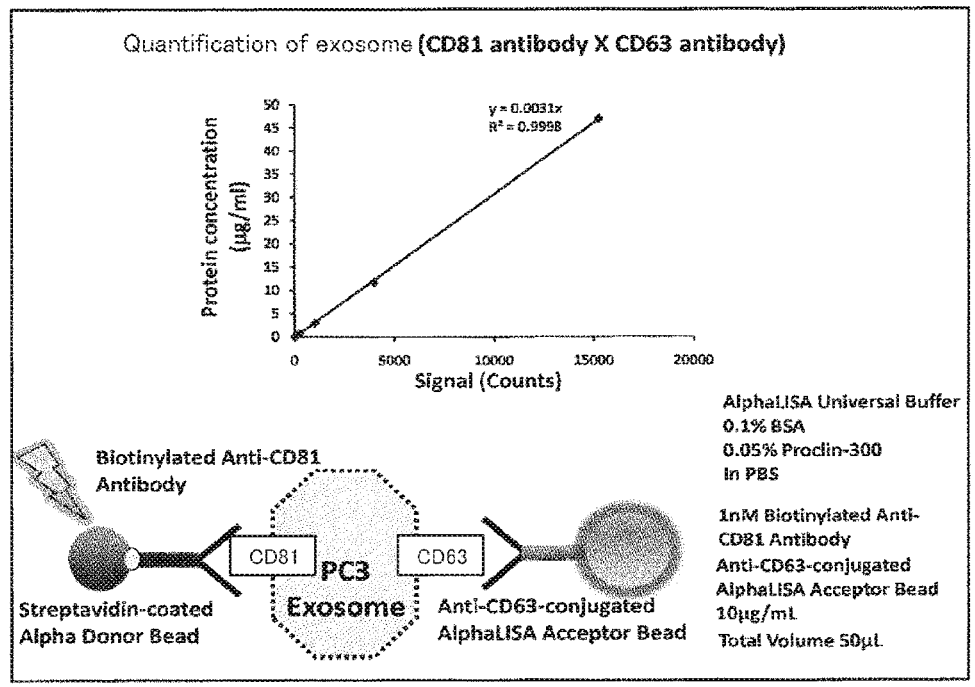
FIG. 2H is a calibration curve used for the quantitative analysis of exosome in Example of the present invention (biotinylated antibody: Purified Mouse Anti-Human CD81, acceptor beads-binding antibody: Purified Mouse Anti-Human CD63).

With respect to FIG. 2H (the combination (6)), Biotinylated Anti-CD81 Antibody having a concentration of 1 nM and Anti-CD63-conjugated AlphaLISA Acceptor Beads having a concentration of 10 μg/mL were added to the aforementioned AlphaLISA Universal Buffer such that the total amount of the solution became 50 μL, and measurement was performed. FIG. 2H shows that Biotinylated Anti-CD81 Antibody that is bound to AlphaScreen streptavidin donor beads (Streptavidin-coated Alpha Donor Beads) and Biotinylated Anti-CD63 Antibody that is bound to Anti-CD63-conjugated AlphaLISA Acceptor Beads are respectively bound to antigen CD81 and antigen CD63 in PC3 exosome. A calibration curve was made by plotting the signal in a horizontal axis and protein concentration (μg/ml) in a vertical axis, and the following equation was obtained: y=0.0031x ($R^2$=0.9998).

Example 1

In this Example, exosome in blood serum was analyzed using blood serum of prostate cancer patients and blood serum of healthy subjects; and the difference between the exosome amount in the blood serum of the prostate cancer patients and the exosome amount in the blood serum of the healthy subjects was examined.

(1) Preparation of Blood Serum

Whole blood was collected from prostate cancer patients (stage 4, n=4) and healthy subjects (n=4), and blood serum was prepared from the whole blood. The amount of the blood serum used in the following exosome analysis was 4 µL.

(2) Analysis of Exosome

Procedures similar to the aforementioned procedures (1) to (4) of "Making of Calibration Curve" in "6. Quantitation of Exosome" were performed so as to prepare reaction solutions each having the composition summarized in Table 1, signals were analyzed in the same manner as the procedure (5), and the obtained signal values were analyzed as the amounts of exosome contained in blood serum.

TABLE 1

| Composition of Reaction Solution (total amount: 50 µL) PBS (AlphaLISA Universal Buffer) | |
|---|---|
| 0.1% | BSA |
| 0.5% | ProClin-300 |
| 1 mg/mL | Dextran-500 |
| 1 nM (nmol/L) | Biotinylated Anti-CD63 Antibody |
| 10 µg/mL | Acceptor beads-binding anti-CD63 antibody |
| 4 µL | Blood serum |

Figure 3:
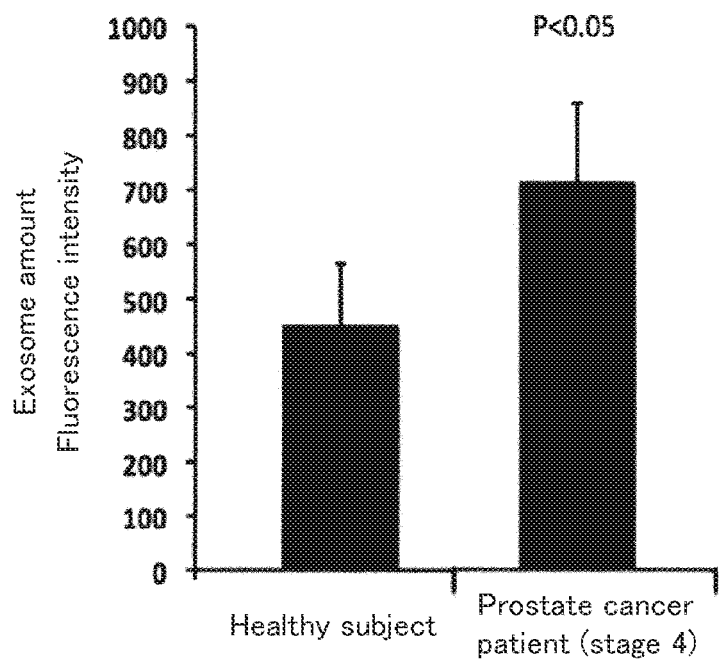
FIG. 3 is a graph showing the analysis result of exosome in blood serum of prostate cancer patients and the analysis result of exosome in blood serum of healthy subjects in Example 1 of the present invention.

The graph of FIG. 3 shows the analysis result of exosome in the both blood serum. As shown in FIG. 3, it was confirmed that blood serum of prostate cancer patients contains significantly more exosome than blood serum of healthy subjects. From this result, it was confirmed that it can be determined whether an analyzed subject is a cancer patient or a healthy subject by analyzing exosome in blood serum. Therefore, according to the present invention, it can be said that exosome in blood can be analyzed in a simple manner, and diagnosis of whether a blood sample donor is a healthy subject or a cancer patient can be conducted, for example.

Example 2

In this Example, exosome in blood serum was analyzed using blood serum of liver cancer patients right after surgery to remove the cancer and blood serum of the same patients after the recurrence, and the difference between the exosome amount in the blood serum right after the surgery to remove the cancer and the exosome amount in the blood serum after the recurrence was examined.

(1) Preparation of Blood Serum

Whole blood of liver cancer patients right after surgery to remove the cancer and whole blood of the same patients after the recurrence were collected, and blood serum was prepared from the whole blood (n=12). The amount of the blood serum used for the following exosome analysis was 4 µL.

(2) Analysis of Exosome

The amount of exosome contained in the blood serum of liver cancer patients right after the surgery to remove the cancer and the amount of exosome contained in the blood serum of the same patients after the recurrence were analyzed in the same manner as in Example 1 except that the blood serum prepared in the above (1) was used.

Figure 4:
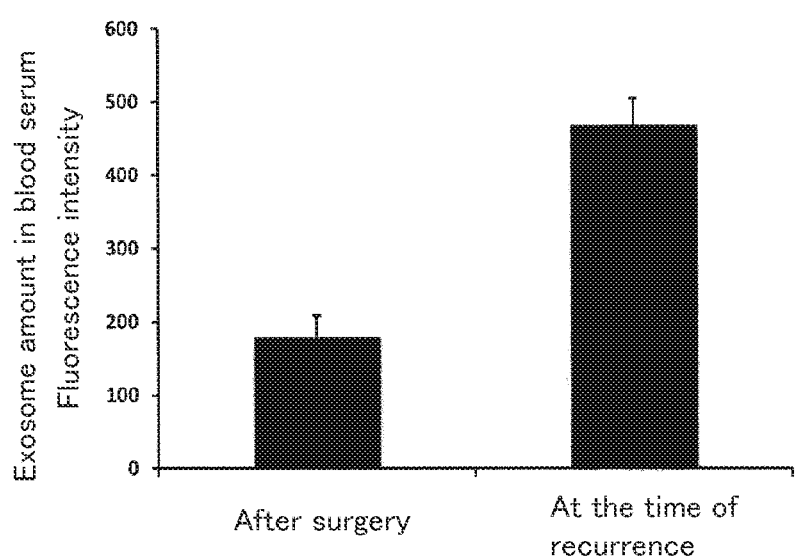
FIG. 4 is a graph showing the analysis result of exosome in blood serum of liver cancer patients right after the surgery to remove the cancer and the analysis result of exosome in blood serum of the same patients at the time of recurrence in Example 2 of the present invention.

The graph of FIG. 4 shows the analysis result of exosome in the both blood serum. As shown in FIG. 4, it was confirmed that blood serum of liver cancer patients after the recurrence contains more exosome than blood serum of the same patients right after the surgery to remove the cancer. From this result, it was confirmed that, with respect to cancer patients who had the surgery to remove the cancer, diagnosis of whether or not the cancer has recurred after the surgery can be conducted by examining exosome in blood serum. Therefore, according to the present invention, for example, with respect to cancer patients, the diagnosis of the recurrence after the surgery to remove the cancer can be conducted by analyzing exosome in blood.

As described above, according to the present invention, exosome in a sample can be analyzed in a simple manner. Therefore, for example, the method of exosome analysis of the present invention is very useful to cancer diagnoses such as whether or not a cancer has occurred, whether or not a cancer has recurred, and the like; and application of the analysis method of the present invention to laboratory testing is greatly expected.

EXPLANATION OF REFERENCE NUMERALS 11 exosome
12, 13 exosome-specific antigen
14, 24 first antibody
15, 25 second antibody
16 excitation label
17 signaling label
18 excitation light
22, 23 cell type-specific antigen

The invention claimed is:

1. A method of quantifying an exosome in a sample, comprising:
   (a) adding to the sample (i) a first monoclonal antibody that specifically binds to a first antigen expressed the exosome and (ii) a second monoclonal antibody that specifically binds to a second antigen expressed on the exosome, to avow the first antibody to bind the first antigen on the exosome and the second antibody to bind the second antigen on the exosome, wherein the first antibody is biotinylated and capable to bind a streptayidin donor bead comprising an excitation label capable to release a singlet oxygen molecule upon light excitation, wherein the second antibody is conjugated to an acceptor bead comprising a signaling label capable to emit a signal in the in the presence of the released singlet oxygen molecule,
   (b) reacting the solution of (a) with (iii) streptavidin donor beads comprising the excitation label to avow the first biotinylated monoclonal antibody to bind the streptavidin donor beads via biotin, to form a reaction solution, wherein the solution of (a) and the reaction solution of (b) do not include a surfactant, wherein the reaction solution of (b) comprises the sample and the first monoclonal antibody bound to the donor bead and bound to the first antigen on the exosome and the second monoclonal antibody bound to the acceptor bead and bound to the second antigen on the exosome,
   (c) irradiating the reaction solution of (b) with excitation light to allow the excitation label to generate a singlet oxygen molecule; and
   (d) measuring a signal emitted from the signaling label, wherein the amount of signal indicates the amount of the exosome in the sample,
   wherein the first and second antigen are exosome specific antigens selected from the group consisting of CD63, CD9, CD81, CD37, CD53, CD82, CD13, CD11, CD86, ICAM-1, Rab5, Annexin V, LAMP1, Caveolin-1, EpCAM, FasL, TRAIL, Galectine3, CD151, Tetraspanin 8, EGFR, HER2, RPN2, CD44, and TGF-13.

2. The method according to claim 1, wherein the sample is blood serum.

3. The method according to claim 1, wherein the amount of the sample is in the range from 1 to 15 μL.

\* \* \* \* \*